(12) United States Patent
Azizian et al.

(10) Patent No.: US 10,849,591 B2
(45) Date of Patent: *Dec. 1, 2020

(54) SYSTEM AND METHOD FOR DYNAMIC VIRTUAL COLLISION OBJECTS

(71) Applicants: INTUITIVE SURGICAL OPERATIONS, INC., Sunnyvale, CA (US); SIEMENS HEALTHCARE GMBH, Bayern (DE)

(72) Inventors: Mahdi Azizian, Santa Clara, CA (US); Jonathan M. Sorger, Belmont, CA (US); Holger Kunze, Bubenreuth (DE); Lutz Blohm, Mohrendorf (DE)

(73) Assignees: INTUITIVE SURGICAL OPERATIONS, INC., Sunnyvale, CA (US); SIEMENS HEALTHCARE GMBH, Bayern (DE)

(*) Notice: Subject to any disclaimer, the term of this patent is extended or adjusted under 35 U.S.C. 154(b) by 157 days.

This patent is subject to a terminal disclaimer.

(21) Appl. No.: 15/956,463

(22) Filed: Apr. 18, 2018

(65) Prior Publication Data

US 2018/0235565 A1 Aug. 23, 2018

Related U.S. Application Data

(63) Continuation of application No. 15/116,561, filed as application No. PCT/US2015/014395 on Feb. 4, 2015, now Pat. No. 9,993,222.

(Continued)

(51) Int. Cl.
*A61B 6/10* (2006.01)
*A61B 6/00* (2006.01)
(Continued)

(52) U.S. Cl.
CPC .............. *A61B 6/547* (2013.01); *A61B 6/102* (2013.01); *A61B 34/20* (2016.02); *B25J 9/1676* (2013.01);
(Continued)

(58) Field of Classification Search
CPC ....... B25J 9/1666; B25J 9/1676; A61B 6/102; G05B 19/4061; G05B 2219/40492;
(Continued)

(56) References Cited

U.S. PATENT DOCUMENTS 4,578,757 A 3/1986 Stark
4,922,430 A * 5/1990 Wavish .................. B25J 9/1666
700/255

(Continued)

FOREIGN PATENT DOCUMENTS

CN 101512453 A 8/2009
GB 2196763 A 5/1988
(Continued)

OTHER PUBLICATIONS

Extended European Search Report for Application No. 15746212.8, dated Oct. 18, 2017, 9 pages.
(Continued)

*Primary Examiner* — Dale Moyer
(74) *Attorney, Agent, or Firm* — Artegis Law Group, LLP (57) ABSTRACT

A system and method of dynamic virtual collision objects includes a control unit for a medical device. The control unit includes one or more processors and an interface coupling the control unit to the medical device. The control unit is configured to determine a position of a first movable segment of the medical device, a volume occupied by the first movable segment being approximated by one or more first virtual collision objects (VCOs); adjust, based on the position and motion goals for the medical device, one or more
(Continued)

properties of the first VCOs; determine, based on the position and the properties, first geometries of the first VCOs; receive second geometries of one or more second VCOs associated with a second segment of a second device; determine relationships between the first VCOs and the second VCOs; and adjust, based on the relationships, a motion plan for the medical device.

20 Claims, 5 Drawing Sheets

Related U.S. Application Data

(60) Provisional application No. 61/936,006, filed on Feb. 5, 2014.

(51) Int. Cl.
| | | |
|---|---|---|
| *B25J 9/16* | (2006.01) | |
| *G05B 19/4061* | (2006.01) | |
| *G16H 40/63* | (2018.01) | |
| *A61B 34/20* | (2016.01) | |

(52) U.S. Cl.
CPC ......... *G05B 19/4061* (2013.01); *G16H 40/63* (2018.01); *A61B 6/4405* (2013.01); *A61B 6/4441* (2013.01); *G05B 2219/40202* (2013.01)

(58) Field of Classification Search
CPC ........... G05B 2219/49145; G05B 2219/49138; G05B 2219/49137; G05B 2219/40476
See application file for complete search history.

(56) References Cited

U.S. PATENT DOCUMENTS

| | | | | |
|---|---|---|---|---|
| 5,056,031 A | * | 10/1991 | Nakano | B25J 9/1676 700/178 |
| 5,347,459 A | * | 9/1994 | Greenspan | B25J 9/1666 345/424 |
| 5,761,391 A | | 6/1998 | Sato et al. | |
| 6,089,742 A | * | 7/2000 | Warmerdam | B25J 9/1666 700/255 |
| 9,993,222 B2 | | 6/2018 | Azizian et al. | |
| 2006/0176001 A1 | * | 8/2006 | Haunerdinger | G05B 19/4061 318/573 |
| 2009/0074252 A1 | * | 3/2009 | Dariush | G11C 11/5621 382/107 |
| 2011/0035053 A1 | | 2/2011 | Guochunxu | |
| 2011/0066282 A1 | | 3/2011 | Bosscher et al. | |
| 2013/0325030 A1 | | 12/2013 | Hourtash et al. | |
| 2014/0277737 A1 | | 9/2014 | Sekiyama et al. | |
| 2015/0005785 A1 | | 1/2015 | Olson | |
| 2015/0328776 A1 | * | 11/2015 | Shiratsuchi | B25J 9/1666 700/255 |
| 2016/0345929 A1 | | 12/2016 | Azizian et al. | |

FOREIGN PATENT DOCUMENTS

| | | |
|---|---|---|
| JP | S58171615 A | 10/1983 |
| JP | S63158620 A | 7/1988 |
| JP | H01224811 A | 9/1989 |
| JP | H02224004 A | 9/1990 |
| KR | 1019990009131 | 2/1999 |
| KR | 100218106 B1 | 9/1999 |
| WO | WO-2008031664 A1 | 3/2008 |
| WO | WO-2013101273 A1 | 7/2013 |
| WO | WO-2014008929 A1 | 1/2014 |

OTHER PUBLICATIONS

International Search Report and Written Opinion for Application No. PCT/US15/14395, dated May 14, 2015, 11 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEM AND METHOD FOR DYNAMIC VIRTUAL COLLISION OBJECTS

RELATED APPLICATIONS

This application is a continuation of U.S. patent application Ser. No. 15/116,561 filed on Aug. 4, 2016 and claims priority to PCT application Serial No. PCT/US15/14395, filed on Feb. 4, 2015, which claims benefit to U.S. Provisional Application Ser. No. 61/936,006 filed on Feb. 5, 2014, each of which is herein incorporated by reference in its entirety.

TECHNICAL FIELD

The present disclosure relates generally to coordinated motion among devices and more particularly to dynamic virtual collision objects.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Many of these electronic devices may be capable of autonomous or semi-autonomous motion of one or more articulated arms and/or end effectors. As these electronic devices move the articulated arms and/or end effectors about a work space, either automatically and/or at the command of an operator, they generally try to avoid collisions between the articulated arms, end effectors, and/or other objects in the work space. Avoiding collisions is important because collisions may often result in damage to the electronic devices, the articulated arms, the end effectors, and/or the other objects in the work space. Collisions may also increase the risk of injury to personnel in the vicinity of the work space and/or patients.

One solution to the collision avoidance problem is to have the operators of the electronic devices, (e.g., medical personnel) monitor and operate each of the electronic devices while maintaining suitable separation distances and/or operate the devices in such a way that they do not interfere with and/or are unable to collide with each other. For example, a computer-assisted surgical device may only be permitted in areas of the operating room where it won't interfere or collide with an imaging system also present in the operating room. Such a restriction may limit the functionality of both the computer-assisted surgical device and the imaging system.

Other approaches include having the electronic devices exchange information regarding their current locations, geometries, and/or planned motions so that each of the devices may stay out of the areas occupied by the other electronic devices. In some instances, this may also include maintaining a safety margin to account for sensor uncertainties, imprecision in control algorithms, and/or the like. These approaches generally take a static approach to the safety margins and provide little or no support for adjusting the safety margins based on changes in the dynamic behavior and/or motion goals of the electronic devices.

Accordingly, it is desirable to provide improved methods and systems for supporting collision avoidance and/or coordinated motion among devices with moving segments.

SUMMARY

Consistent with some embodiments, a control unit for a medical device includes one or more processors and an interface coupling the control unit to the medical device. The control unit is configured to determine a position of a first movable segment of the medical device, a volume occupied by the first movable segment being approximated by one or more first virtual collision objects (VCOs); adjust, based on the position and motion goals for the medical device, one or more properties of the first VCOs; determine, based on the position and the properties, first geometries of the first VCOs; receive second geometries of one or more second VCOs associated with a second segment of a second device; determine relationships between the first VCOs and the second VCOs; and adjust, based on the relationships, a motion plan for the medical device.

Consistent with some embodiments, a method of controlling motion in a medical device includes determining by a control unit a position of a first segment of the medical device, the control unit being coupled to the medical device by an interface; adjusting, based on the position and motion goals for the medical device, one or more properties of one or more first VCOs associated with the first segment; determining, based on the position and the properties, first geometries of the first VCOs; receiving second geometries of one or more second VCOs associated with a second device; determining relationships between the first VCOs and the second VCOs; and adjusting, based on the relationships, a motion plan for the medical device.

Consistent with some embodiments, a coordinated motion system includes a first control unit coupled to a first medical device via a first interface and a second control unit coupled to a second medical device via a second interface. The first control unit is configured to determine a first position of a first segment of the first medical device; adjust, based on the first position and first motion goals for the first medical device, one or more first properties of one or more first VCOs associated with the first segment; determine, based on the first position and the first properties, first geometries of the first VCOs; send the first geometries of the first VCOs to the second control unit; receive second geometries of one or more second VCOs associated with a second segment of the second medical device from the second control unit; determine first relationships between the first VCOs and the second VCOs; and adjust, based on the first relationships, a first motion plan for the first medical device. The second control unit is configured to determine a second position of the second segment; adjust, based on the second position and second motion goals for the second medical device, one or more second properties of the second VCOs; determine, based on the second position and the second properties, the second geometries of the second VCOs; send the second geometries to the first control unit; receive the first geometries from the first control unit; determine second relationships between the first VCOs and the second VCOs; and adjust, based on the second relationships, a second motion plan for the second medical device. The first motion plan and the second motion plan include coordinated motion between the first medical device and the second medical device.

BRIEF DESCRIPTION OF THE DRAWINGS

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
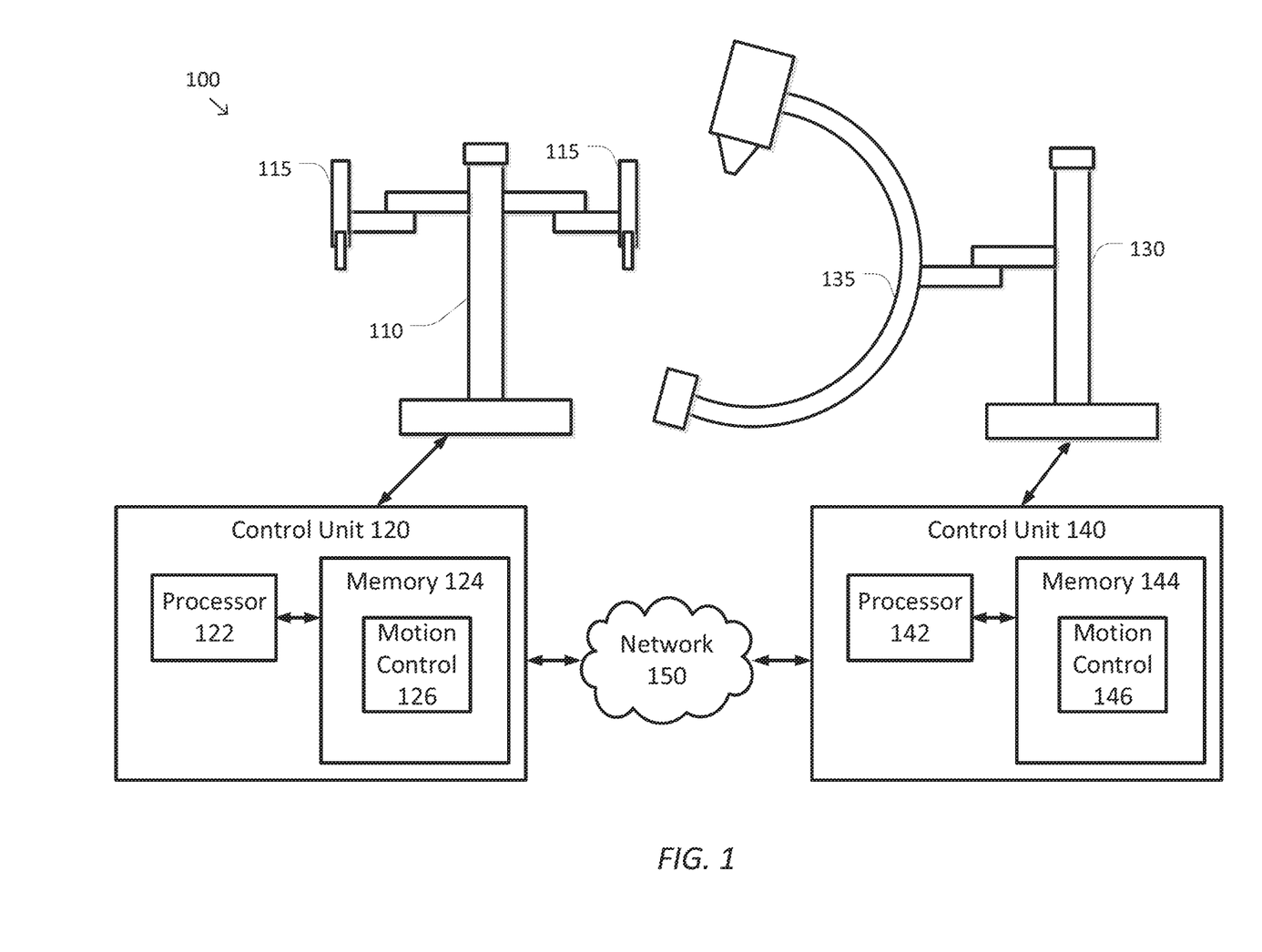
FIG. 1 is a simplified diagram of a coordinated motion system according to some embodiments.

FIG. 1 is a simplified diagram of a coordinated motion system 100 according to some embodiments. As shown in FIG. 1, coordinated motion system 100 includes a device 110 with one or more movable arms and/or one or more end effectors. In some examples, device 110 may be consistent with a computer-assisted surgical device. Device 110 may include one or more movable segments or articulated arms 115 for supporting surgical instruments, imaging devices, and/or the like. Device 110 may further be coupled to an operator workstation (not shown), which may include one or more master controls for operating the device 110 and/or the one or more articulated arms 115. In some embodiments, device 110 and the operator workstation may correspond to a da Vinci® Surgical System commercialized by Intuitive Surgical, Inc. of Sunnyvale, Calif. In some embodiments, computer-assisted surgical devices with other configurations, fewer or more articulated arms, and/or the like may be used with coordinated motion system 100.

Device 110 is coupled to a control unit 120 via an interface. Control unit 120 includes a processor 122 coupled to memory 124. Operation of control unit 120 is controlled by processor 122. And although control unit 120 is shown with only one processor 122, it is understood that processor 122 may be representative of one or more central processing units, multi-core processors, microprocessors, microcontrollers, digital signal processors, field programmable gate arrays (FPGAs), application specific integrated circuits (ASICs), and/or the like in control unit 120. Control unit 120 may be implemented as a stand-alone subsystem and/or board added to a computing device or as a virtual machine. In some embodiments, control unit may be included as part of the operator workstation and/or operated separately from, but in coordination with the operator workstation.

Memory 124 may be used to store software executed by control unit 120 and/or one or more data structures used during operation of control unit 120. Memory 124 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 124 includes a motion control application 126 that may be used to support autonomous and/or semiautonomous control of device 110. Motion control application 126 may include one or more application programming interfaces (APIs) for receiving position and/or motion information from device 110, exchanging position, motion, and/or collision avoidance information with other control units regarding other devices, and/or planning and/or assisting in the planning of motion for device 110, articulated arms 115, and/or the end effectors of device 110. And although motion control application 126 is depicted as a software application, motion control application 126 may be implemented using hardware, software, and/or a combination of hardware and software.

Coordinated motion system 100 may further include a device 130 with a different configuration of one or more movable arms and/or one or more end effectors than device 110. In some examples, device 130 may be consistent with an imaging device that includes an imaging subsystem 135 that may be used to take one or more images of a patient and/or other object located in the work space of coordinated motion system 100. Device 130 and imaging subsystem 135 may include one or more movable elements used to position the imaging subsystem 135 to take the desired one or more images. Although device 130 in FIG. 1 is depicted with imaging subsystem 135 characterized as a C-arm, other types of imaging devices are possible in coordinated motion system 100. In some embodiments, imaging subsystem 135 may include a donut-shaped bore such as an MR-bore, an articulated arm with a probe, one or more articulated arms, and/or the like. In some embodiments, device 130 may also be coupled to an operator workstation (not shown) that may be the same or a different operator workstation than the operator workstation used for device 110.

Similar to device 110, device 130 is coupled to a control unit 140 via an interface. Control unit 140 includes a processor 142 coupled to memory 144. Operation of control unit 140 is controlled by processor 142. And although control unit 140 is shown with only one processor 142, it is understood that processor 142 may be representative of one or more central processing units, multi-core processors, microprocessors, microcontrollers, digital signal processors, FPGAs, ASICs, and/or the like in control unit 140. Control unit 140 may be implemented as a stand-alone subsystem and/or board added to a computing device or as a virtual machine. In some embodiments, control unit may be included as part of the operator workstation and/or operated separately from, but in coordination with the operator workstation.

Memory 144 may be used to store software executed by control unit 140 and/or one or more data structures used during operation of control unit 140. Memory 144 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 144 includes a motion control application 146 that may be used to support autonomous and/or semiautonomous control of device 110. Motion control application 146 may include one or more APIs for receiving position and/or motion information from device 120, exchanging position, motion, and/or collision avoidance information with other control units (e.g., control unit 120) regarding other devices (e.g., device 110), and/or planning and/or assisting in the planning of motion for device 130 and/or imaging subsystem 135. And although motion control application 146 is depicted as a software application, motion control application 146 may be implemented using hardware, software, and/or a combination of hardware and software.

Control units 120 and 140 may be coupled together using a network 150. Network 150 may be any type of network that includes one or more connectors and/or cables, one or more local area networks (LANs) such as an Ethernet, and/or one or more wide area networks (WANs) such as an internet. In some examples, network 150 may include one or more computing devices to support the exchange of position, motion, and/or collision avoidance information between control units 120 and 140. In some examples, the one or more computing devices may support a shared interface, such as the shared interface described in U.S. Provisional Patent Application No. 61/866,949, entitled "System and Method for Coordinated Motion Among Heterogeneous Devices", by Mandi Azizian, Jonathan Sorger, and Simon DiMaio, filed on Aug. 16, 2013, the contents of which are herein incorporated by reference in their entirety, for all purposes.

In some embodiments, coordinated motion system 100 may be found in an operating room and/or an interventional suite. And although coordinated motion system 100 shows only two devices 110 and 130, one of ordinary skill would understand that coordinated motion system 100 may include any number of devices with movable arms and/or end effectors of similar and/or different design from devices 110 and 130. In some examples, each of the devices may have fewer or more movable arms and/or end effectors.

In some embodiments, different arrangements and/or configurations may be used in coordinated motion system 100. In some examples, a control unit may be responsible for controlling the motion of more than one device. In some examples, the control units may form a master-slave hierarchy in which one of the control units may direct the motion planning and/or motion control provided by one or more of the other control units.

Numerous techniques and approaches have been used over the years to support collision avoidance in systems with one or more devices having one or more movable elements, such as one or more articulated arms and/or end effectors. One such approach is the use of virtual collisions objects (VCOs) that may be used to approximate the volumes occupied by respective devices and/or objects. In many applications, a VCO may be a virtual shape that circumscribes part or all of a device or object. Each VCO may be centered about a portion of the device or object and may be based on a shape that may be easily parameterized. For example, U.S. Pat. No. 4,578,757 describes the use of spherically-shaped VCOs that are located at intervals along independently movable bodies. The spherically-shaped VCOs are positioned and sized so that the sub-volumes occupied by the movable bodies are entirely contained in the sub-volumes occupied by the spherically-shaped VCOs. Because of this containment relationship among the sub-volumes, as long as the sub-volumes occupied by the VCOs of the respective movable bodies do not overlap then there is no collision between the movable bodies. Use of spheres for the VCOs may also simplify the collision computations because overlap between two spherical VCOs may be determined by comparing the distance between the center points of the two VCOs to the sum of the radii of the two VCOs.

Figure 2:
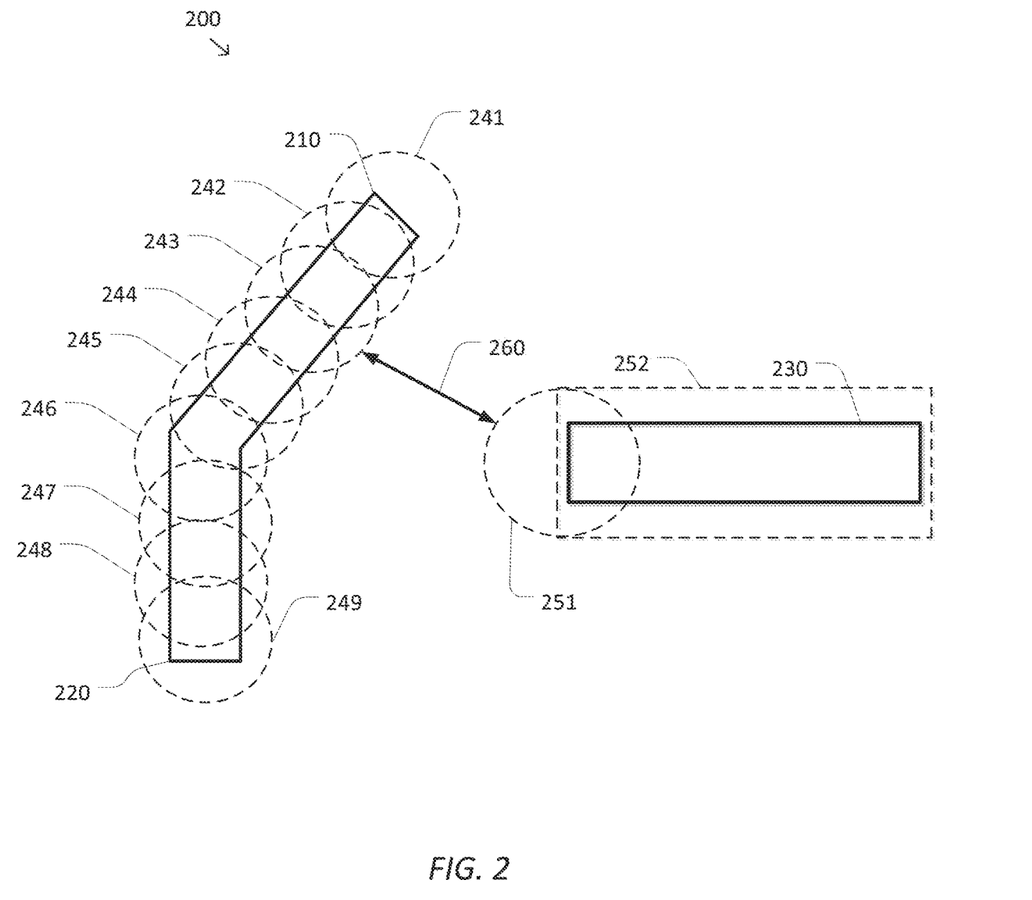
FIG. 2 is a simplified diagram showing the use of virtual collision objects in a work space according to some embodiments.

FIG. 2 is a simplified diagram showing the use of virtual collision objects in a work space 200 according to some embodiments. As shown in FIG. 2, a first device includes a segment 210 coupled to a segment 220. Although not shown, segments 210 and 220 may be movable relative to each other, such as via a rotational joint, and/or movable about work space 200. FIG. 2 also shows a second device that includes a segment 230. Segment 230 may also be capable of movement relative to and independently of segments 210 and 220. In some examples, segments 210 and 220 may be part of device 110 and segment 230 may be part of device 130. In some examples, one or more of segments 210-230 may be stationary and represent part or all of an object and/or a device in work space.

Because of the somewhat complex geometry of segments 210-230, which are depicted simplistically as rectangular bodies, it may be advantageous to enhance the modeling of segments 210-230 using one or more VCOs. As shown in FIG. 2, segments 210 and 220 are shown with nine associated VCOs 241-249. Each of the VCOs 241-249 is characterized as a spherical shape centered about some portion of segments 210 and 220. Collectively, the sub-volumes occupied by VCOs 241-249 circumscribe the sub-volumes occupied by segments 210 and 220. The ability of VCOs 241-249 to finely model the sub-volume occupied by segments 210 and 220 may be controlled by altering the number of VCOs 241-249 and/or altering the sizes of VCOs 241-249 relative to the sizes of segments 210 and 220. In some examples, fewer VCOs 241-249 may be used to reduce computational costs, but with correspondingly poorer modeling of segments 210 and 220 and with VCOs 241-249 generally occupying a larger sub-volume about segments 210 and 220, which may not be desirable. Segment 230 is shown with a different pattern of VCOs including a spherical VCO 251 at the left end of segment 230 and a cylindrical VCO 252 along the length of segment 230. The use of non-spherical VCOs, such as cylindrical VCO 252 may be used as a tradeoff between modeling complexity and the use of fewer VCOs for a segment or group of segments. In some examples, it may be desirable to limit the shapes of VCOs to easily modeled or parameterized shapes such as spheres, cylinders, rectangular solids, ovoids, capsules (cylinders with hemispherical ends), and/or the like.

In some embodiments, VCOs 241-249 and 251 and 252 may be used to support collision avoidance between segments 210-230. In some examples, the simpler geometries of VCOs 241-249 and 251 and 252 may be used as a pre-test to determine whether there may be a collision and/or an imminent collision between segments 210-230. As long as there is no overlap between the sub-volumes occupied by VCOs 241-249 and VCOs 251 and 252, there should be no collision between segments 210 and 220 and segment 230. In some examples, a closest distance 260 between VCOs 241-249 and VCOs 251 and 252 may provide an indication of the likelihood of a collision. The size of distance 260 may provide a rough estimate of how close segments 210 and 220 are to segment 230. In some examples, when the size of distance 260 is decreasing this may also indicate a higher likelihood of an impending collision. In some examples, the control units, such as control units 120 and/or 140, may exchange information regarding the location and size of VCOs 241-249 and/or 251 and 252 to support their own collision avoidance computations and/or to use the sub-volumes occupied by VCOs 241-249 and 251 and 252 as no-fly/stay away zones for their own respective motion planning.

In some embodiments, VCOs 241-249 and/or 251 and 252 may provide support for other motion-related operations. In some examples, VCOs 241-249 and/or 251 and 252 may be used to provide a safety or error margin when determining a position for the segments 210-230. When the precise location of segments 210-230 may not be known due to sensor uncertainties, imprecision in control algorithms, and/or the like, the use of VCOs 241-249 and/or 251 and 252 may reserve sufficient space about segments 210-230 to avoid collision and/or other unwanted consequences. In some examples, when segments 210 and 220 become close enough to segment 230 so that one or more of VCOs 241-249 overlap one or more of VCOs 251 and 252, this may trigger use of one or more different motion control algorithms that provide for finer and/or more delicate control of segments 210-230.

Figure 3:
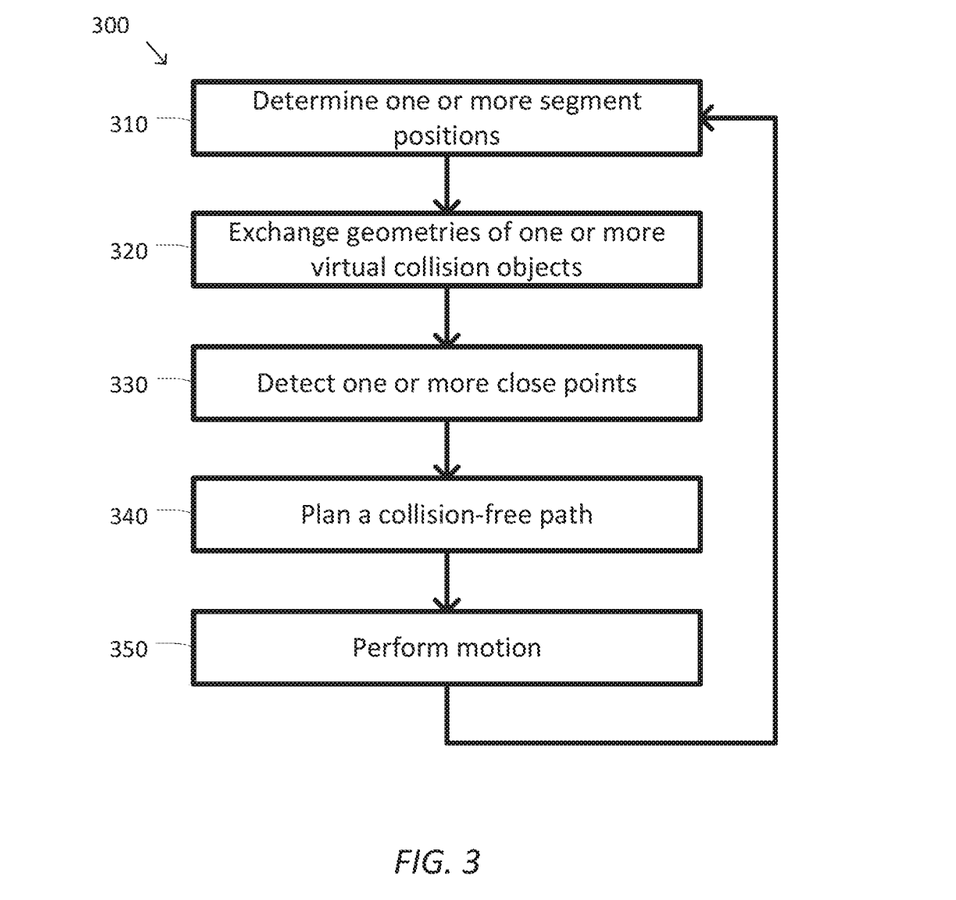
FIG. 3 is a simplified diagram of a method of collision avoidance according to some embodiments.

FIG. 3 is a simplified diagram of a method 300 of collision avoidance according to some embodiments. One or more of the processes 310-350 of method 300 may be implemented, at least in part, in the form of executable code stored on non-transient, tangible, machine readable media that when run by one or more processors (e.g., the processors 122 and/or 142 in control units 120 and/or 140, respectively) may cause the one or more processors to perform one or more of the processes 310-350. In some embodiments, the method 300 may be performed by an application, such as motion control applications 126 and/or 146.

At a process 310, one or more segment positions are determined. A control unit may determine the positions of one or more segments of a device that the control unit is controlling. In some examples, control unit 120 may determine the positions of one or more segments associated with the one or more articulated arms 115 and/or end effectors of device 110. In some examples, control unit 140 may determine the positions of one or more segments associated with the imaging subsystem 135 of device 130. The control unit may use one or more joint sensors to determine the relative positions and/or rotations of the various joints between the segments in the device that is being controlled. In some examples, the joint sensors may include potentiometers, optical encoders, and/or the like. In some examples, the information from the joint sensors may be combined with one or more kinematic models of the device and its segments to determine the one or more segment positions. In some examples, the control unit may determine the one or more segment positions based on information obtained from one or more images taken of the segments and/or the device being controlled. In some examples, the one or more segment positions may be determined in a local coordinate system and/or translated to a global coordinate system.

At a process 320, geometries of one or more VCOs are exchanged. Using the one or more segment positions determined during process 310, the control unit may determine the geometries (e.g., the locations and/or orientations) of the one or more VCOs associated with the one or more segments. For example, when the control unit is controlling the device containing segments 210 and 220, the positions of segments 210 and 220 may be used to determine the geometries of VCOs 241-249. Similarly, when the control unit is controlling the device containing segment 230, the positions of segment 230 may be used to determine the geometries of VCOs 251 and 252. The control unit may then share the geometries of these VCOs with other control units responsible for controlling other devices with movable segments. The control unit may also receive information regarding the geometries of the movable segments of the other devices. In some examples, the control unit may exchange the geometries of the VCOs by exchanging one or more messages using a network, such as network 150, through a shared interface, and/or the like. In some embodiments, the exchange of the geometries of the VCOs may include exchanging a time series of geometries that correspond to past, present, and/or planned motions.

At a process 330, one or more close points are detected. Using the geometries of the VCOs determined and/or exchanged during process 320, the control unit may detect one or more close points between the segments of the device being controlled and the segments of other devices for which VCO geometry information is known. The one or more close points may indicate areas of potential collision, areas to avoid during motion planning, areas for which more detailed geometry modeling is desirable, and/or the like. In some examples, the one or more close points may include distance 260.

At a process 340, a collision-free path is planned. Using the geometries of the VCOs determined and/or exchanged during process 320 and/or the one or more close points detected during process 330, the control unit may determine a collision-free path for the segments of the device it is controlling. In some examples, the collision-free path may use one or more kinematic models of the segments of the device being controlled. In some examples, the path or motion planning may use the geometries of the VCOs received during process 320 as no-fly/stay away zones that the VCOs of the segments of the device being controlled may not overlap. In some examples, distances between the geometries of the VCOs may be kept above a minimum threshold and/or maximized to further reduce the possibility of a collision using the planned paths. In some examples, the end position of the path may correspond to a desired position and/or orientation of one or more end effectors of the device being controlled.

At a process 350, motion is performed. Using the paths planned during process 340, the control unit may direct one or more movement commands to the actuators of the device being controlled. The one or more actuators may then move the segments of the device being controlled consistent with the planned paths. In some examples, this may include adjusting one or more currents and/or voltages supplied to the actuators.

As the motion plan is being performed during process 350, this may result in changes in the position of the segments of the device being controlled. Thus, method 300 may periodically repeat so that the motion being performed is being continually updated to reflect changes in the positions, orientations, and/or movement of each of the segments of the various devices that are relevant to the movement of the device being controlled.

The collision avoidance of method 300 uses a generally static model for the VCOs associated with the various segments. This is because collision avoidance between the segments of two or more devices may be effectively accomplished using a static no-fly/stay away model of segment geometry. The relationships between the geometries of VCOs of different devices and segments generally provides a good test for collision detection by looking for overlaps between VCOs, supports a useful safety margin around the segments by creating circumscribing volumes, and/or provides support for imminent collision prediction by examining close points and trends in close point distances. However, this static model of VCOs may limit their usefulness.

By making dynamic adjustments to one or more properties of the VCOs used to model a segment, additional and/or more powerful collision avoidance and coordinated motion algorithms may be supported. The one or more properties may include the size, shape, number, resiliency of the VCOs, and/or the like. By dynamically adjusting one or more of these properties, the VCOs may be used to model changes in motion goals, adapt to changes in motion characteristics, induce changes in the motion behavior of other nearby devices and segments, provide feedback to device operators, and/or the like.

In some embodiments, dynamically changing the size of VCOs may aid other motion algorithms in adjusting to changes in motion goals and/or motion characteristics. In some examples, the momentum of a segment in a device increases with the velocity at which the segment is moving. The higher the momentum of the device, the harder it becomes for the actuators to change the velocity of the segment, such as to prevent a collision once an impending collision is detected. By increasing the size of the VCOs associated with the segment to reflect this increase in momentum, it is possible to effectively introduce additional safety margin about the fast moving segment so as to provide earlier warnings before collisions may occur. This is because the larger VCOs are more likely to overlap the VCOs of other segments earlier than would smaller VCOs. In some examples, this change in size may also be accompanied by a reduction in the number of VCOs associated with the segment.

In some examples, reducing the sizes of the VCOs associated with a segment may permit better use of fine motion and/or close operation with segments in other devices. When the size of the VCOs is reduced to more closely match the volumes of the associated segment, it is possible to use the generally more efficient collision avoidance tests associated with the VCOs during fine motion and/or close operation. This may help improve the computational efficiency associated with fine motion and/or close operation of the segment and the corresponding device. In some examples, the reduction in size of the VCOs may also result in an increase in the number of VCOs associated with the segment and/or the shape of the VCOs so that they may more closely match the geometry of the segment.

In some embodiments, dynamically changing the size of VCOs may allow one device to induce changes in motion behavior of other devices. In some examples, the increase of VCO sizes during higher velocity motion may provide earlier warnings to other devices that are associated with the earlier collision warnings. In some examples, rapidly increasing the size of one or more VCOs associated with a segment may induce an emergency stop and/or an emergency retreat in another device. As the sizes of the VCOs rapidly increase, this may trigger one or more collision alerts in other devices as those devices find it either impossible to avoid a collision and/or to effectively move away from the very large VCOs. If the VCOs become large enough (e.g., as large as a work space), they may be used to induce an emergency stop in other devices in the work space. In some examples, one or more VCOs associated with a segment may be expanded to touch other VCOs. In this approach, each of the VCOs may be rapidly expanded to the point to just before they overlap with the nearest VCO of a segment in another device. In this way the maximum amount of maneuvering space may be claimed around a segment. In some examples, the close point distance between two VCOs, such as distance 260 between VCOs 243 and 251, may be used to determine the desired expansion size of the VCO that is being expanded to touch, such as by adding the close point distance to the radius of the VCO.

In some embodiments, dynamically changing the size, shape, and/or number of the VCOs associated with a segment may be useful in better modeling of changes in the shapes of segments and/or the changes in the joint angles, positioning, and/or relative orientations of segments within the same device. In some examples, these changes in size, shape, and/or number may be useful for taking advantage of the computational efficiency associated with the use of VCOs with the ability of the VCOs to more effectively approximate the geometries of the respective segments.

In some embodiments, VCOs may be used to protect one or more volumes of a workspace. In some examples, one or more VCOs may be used to reserve an operational volume for one or more segments in a device. The one or more VCOs may be fixed or movable within the workspace and provide the operational volume that other segments in other devices are discouraged and/or prevented from entering. These one or more VCOs may move with the one or more segments or may move independently of the one or more segments. In some examples, one or more dynamic VCOs may create stay out, no-fly, and/or protected regions for other objects in the workspace. In some examples, the one or more dynamic VCOs may protect a portion of a patient's anatomy and/or objects in the workspace. In some examples, the protected anatomy may create margins around a tumor, one or more organs, and/or the like. In some examples, the one or more dynamic VCOs may be modeled based on one or more images taken of the patient's anatomy. In some examples, the one or more dynamic VCOs may be changed as the patient moves and/or other metabolic processes take place, such as expanding and contracting around a beating heart and/or a respirating lung.

In some embodiments, VCOs may also be used to provide more complex influences on motion beyond those associated with collision-like activities. In some examples, by modeling VCOs as deformable objects with resiliency, it is possible for the VCOs of one segment to impart a virtual displacing force on the VCOs of other segments. In some examples, this virtual displacing force may be used to push the other segments away and thus induce collision avoidance behavior in those other segments. In some examples, this virtual displacing force may be used to provide haptic and/or other feedback to an operator to discourage the operator from continuing undesirable motion. In some examples, the virtual displacing force may also trigger emergency stop behavior when it exceeds a threshold. In some examples, the virtual displacing force may be used to induce compliant motion where a motion goal may be to maintain the virtual displacing force at a predetermined value. In some examples, the resiliency of a VCO may be dynamically changed to provide different levels of virtual displacing force under different circumstances. In some examples, the resiliency may be increased in VCOs associated with segments that are given positional priority and are not to be as easily displaced from a desired position and/or motion as segments in other devices. In some examples, the resiliency may be increased in collision and/or near collision situations to increase feedback and/or motion resistance in nearby segments in the other devices.

Figure 4:
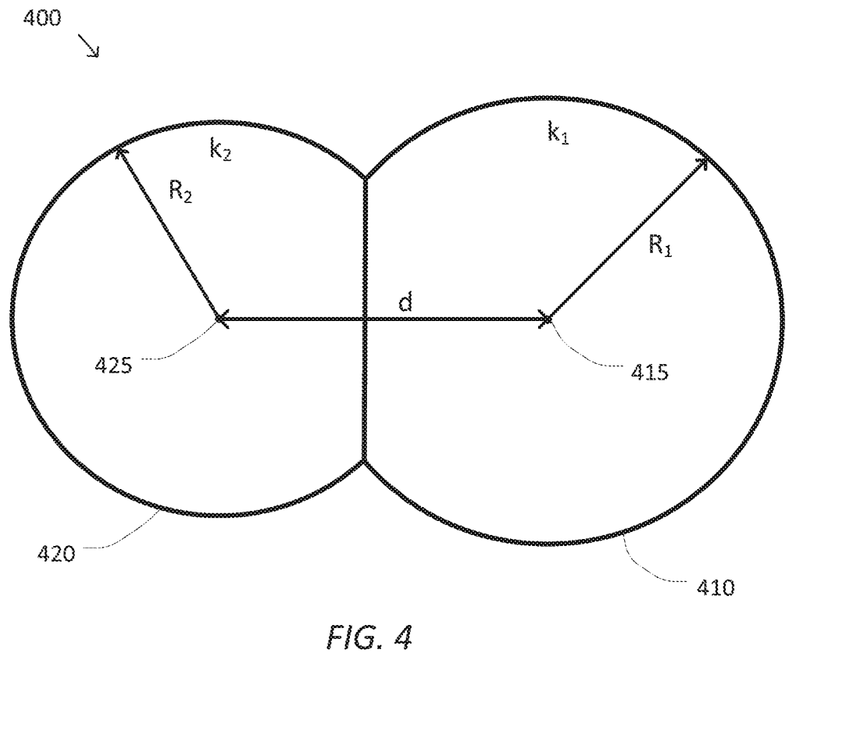
FIG. 4 is a simplified diagram of interaction between resilient virtual collision objects according to some embodiments.

FIG. 4 is a simplified diagram of interaction between resilient virtual collision objects according to some embodiments. As shown in FIG. 4, a first resilient VCO 410 with radius $R_1$ and coefficient of resiliency $k_1$ is interacting with a second resilient VCO 420 with a radius $R_2$ and coefficient of resiliency $k_2$. Resilient VCOs 410 and 420 are interacting because the distance d between a center 415 of resilient VCO 410 and a center 425 of resilient VCO 420 is less than $R_1+R_2$ so that there would be an overlap between the uncompressed sub-volumes associated with resilient VCOs 410 and 420. Any of several models may be used to determine the virtual displacing force being applied by resilient VCOs 410 and 420 on each other. Equation 1 shows one such model where the virtual displacing force is modeled in three zones.

$$F = \begin{cases} 0 & d \geq R_1 + R_2 \\ \dfrac{Kk_1 k_2}{(d - d_{min} + \delta)^2} & d_{min} < d < R_1 + R_2 \\ \text{Stop} & d \leq d_{min} \end{cases} \quad (1)$$

In a first zone, where there is no overlap in the uncompressed sub-volumes associated with resilient VCOs 410 and 420 (i.e., where d is greater than or equal to $R_1+R_2$) there is no virtual displacing force. In a second zone, where overlap begins, the virtual displacing force increases inversely with respect to the distance d. In some examples, the square of the distance may be used for more efficient computation. The constant of proportionality K may be set to control the scale of the virtual displacing force. The value of $d_{min}$ may be set to any threshold either as a fixed value and/or may be set as a percentage of $R_1+R_2$, such as ten, twenty, fifty, or some other percent of $R_1+R_2$ to set a minimum close point. In some examples, $d_{min}$ may be set based on the sizes of the respective segments being approximated by the VCOs 410 and 420. The value of $\delta$ may be set to a nominally small value to prevent a division by zero error in the equation. And, in a third zone, the virtual displacing force reaches a maximum amount that is interpreted as an emergency stop situation when d drops below $d_{min}$, reflecting very close proximity between the underlying segments. As with other aspects of VCO modeling, the values of $d_{min}$, $\delta$, $k_1$, $k_2$, and K may be set dynamically.

In some embodiments, the formula for F may be altered in the second zone to account for only the virtual displacing force applied by the other resilient VCO. For example, the virtual displacing force applied by resilient VCO 420 on resilient VCO 410 would include $k_2$ in the equation and $k_1$ would be omitted as shown in Equation 2.

$$F \text{ of VCO 420 on VCO 410} = \begin{cases} 0 & d \geq R_1 + R_2 \\ \dfrac{Kk_2}{(d - d_{min} + \delta)^2} & d_{min} < d < R_1 + R_2 \\ \text{Stop} & d \leq d_{min} \end{cases} \quad (2)$$

The examples of Equations 1 and 2 are representative only and other modeling approaches may be used to determine the virtual displacing force. In some embodiments, the equations for virtual displacing force may be adapted to other than spherical resilient VCOs, such as cylinders, ovoids, capsules, rectangular solids and the like. In some embodiments, the coefficient of resiliency for a resilient VCO may be non-isotropic and/or non-homogenous. In some examples, the coefficient of resiliency may vary based on the geometry of the VCO, such as a higher coefficient of resiliency along the radii of a cylindrical VCO than the coefficient of resiliency along the axis. In some examples, the coefficient of resiliency may be higher in a direction of movement of the associated segment so as to provide a higher virtual displacing force along the direction of movement as that direction may have a higher likelihood of an impending collision. In some examples, the coefficient of resiliency may be modeled as a vector and/or tensor field applied to the volume of the resilient VCO. In some embodiments, gas and/or fluid dynamic models may be used to determine the virtual displacing force as if the VCOs were filled with gasses and/or gels. In some embodiments, the VCOs may be modeled as a volume filled with pellets and/or other small objects that may be either rigid or deformable. In some embodiments, finite element models may be used to determine the virtual displacing force. In some embodiments, the coefficient of resiliency may be negative to create a virtual attracting force to encourage movement of one or more segments into a desired position and/or pose.

Figure 5:
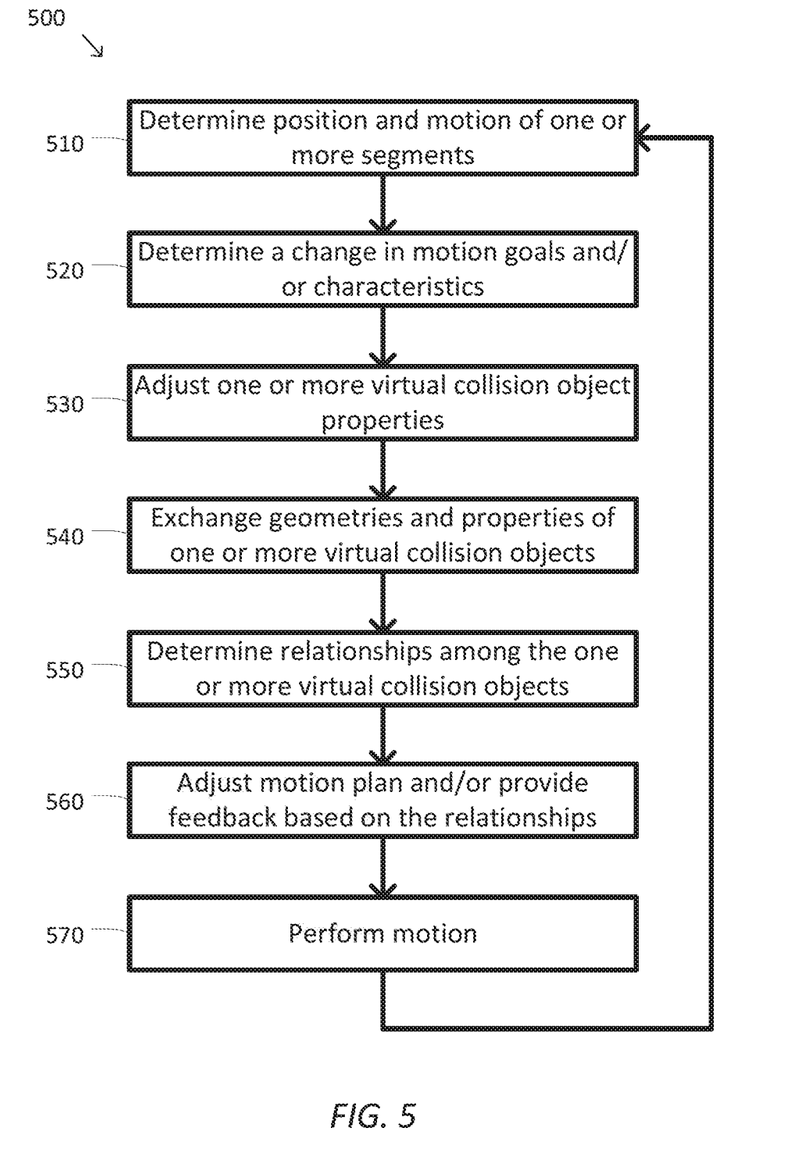
FIG. 5 is a simplified diagram of a method of coordinated motion according to some embodiments.

FIG. 5 is a simplified diagram of a method 500 of coordinated motion according to some embodiments. One or more of the processes 510-570 of method 500 may be implemented, at least in part, in the form of executable code stored on non-transient, tangible, machine readable media that when run by one or more processors (e.g., the processors 122 and/or 142 in control units 120 and/or 140, respectively) may cause the one or more processors to perform one or more of the processes 510-570. In some embodiments, the method 500 may be performed by an application, such as motion control applications 126 and/or 146.

At a process 510, position and/or motion of one or more segments is determined. A control unit may determine the position and/or motion of one or more segments of a device that the control unit is controlling. In some examples, control unit 120 may determine the position and/or motion of the one or more segments associated with the one or more articulated arms 115 and/or end effectors of device 110. In some examples, control unit 140 may determine the position and/or motion of one or more segments associated with the imaging subsystem 135 of device 130. The control unit may use one or more joint sensors to determine the relative positions and/or rotations of the various joints between the segments in the device that is being controlled. In some examples, the joint sensors may include potentiometers, optical encoders, and/or the like. In some examples, the information from the joint sensors may be combined with one or more kinematic models of the device and its segments to determine the one or more segment positions. In some examples, the control unit may determine the one or more segment positions based on information obtained from one or more images taken of the segments and/or the device being controlled. In some examples, the one or more segment positions may be determined in a local coordinate system and/or translated to a global coordinate system. In some examples, joint velocities in conjunction with the one or more kinematic models may be used to determine the relative motions of the one or more segments. In some examples, numerical differentiation techniques may be used to determine the motion of the one or more segments based on one or more positions of the one or more segments recorded over time.

At a process 520, a change in motion goals and/or characteristics may be determined. Based on the desired motion goals of the one or more segments in the device being controlled, it may be appropriate to alter the properties of one or more VCOs associated with the one or more segments. In some examples, the motions determined during process 510 may be used to determine a velocity of the one or more segments that may be used to adjust one or more safety margins. In some examples, the motions determined during process 510 may be combined with a model of the mass of the one or more segments to determine a momentum of the one or more segments that may be used to adjust the one or more safety margins. In some examples, a switch to a fine motion and/or a close operation may be used to adjust a size, shape, and/or number of VCOs associated with one or more of the segments.

In some examples, changes in the relative orientations of the one or more segments may be used to adjust a size, shape, and/or number of VCOs associated with one or more of the segments. In some examples, a desire to implement an emergency stop and/or an expand to touch may be made as part of a control strategy. In some examples, the changes to the motion goals and/or the characteristics may be provided by an operator and/or an application using the device being controlled.

At a process 530, one or more virtual collision object properties are adjusted. Based on the changes in motion goals and/or motion characteristics determined during process 520, one or more virtual collision object properties are adjusted. This may include changing a size, shape, number, and/or resiliency of any of the VCOs associated with the segments of the device being controlled. In some examples, the size of one or more VCOs may be scaled based on the determined velocities and/or momentums, to implement an emergency stop, and/or to implement an expand to touch. In some examples, the size, shape, and/or number of VCOs may be changed to support changes in the relationships among the one or more segments, to switch to or from fine motion or close operation, and/or to adapt to changes in other properties of the VCOs. In some examples, the resiliency of one or more of the VCOs may be adjusted make a corresponding segment less or more susceptible to motion cues received from the VCOs of segments in other devices.

At a process 540, geometries and properties of one or more VCOs are exchanged. Using the one or more segment positions determined during process 510 and both the changed and unchanged properties of the VCOs, the control unit may determine the geometries (e.g., the locations and/or orientations) of the one or more VCOs associated with the one or more segments. For example, when the control unit is controlling the device containing segments 210 and 220, the positions of segments 210 and 220 and/or the properties of VCOs 241-249 may be used to determine the geometries of VCOs 241-249. Similarly, when the control unit is controlling the device containing segment 230, the positions of segment 230 and/or the properties of VCOs 251 and 252 may be used to determine the geometries of VCOs 251 and 252. The control unit may then share the geometries and properties of these VCOs with other control units responsible for controlling other devices with movable segments. The control unit may also receive information regarding the geometries and properties of the movable segments of the other devices. In some examples, the control unit may exchange the geometries and properties of the VCOs by exchanging one or more messages using a network, such as network 150, through a shared interface, and/or the like. In some embodiments, the exchange of the geometries and properties of the VCOs may include exchanging a time series of geometries and/or properties that correspond to past, present, and/or planned motions.

At a process 550, relationships among the one or more virtual collision objects are determined. The geometries and/or properties of the one or more VCOs exchanged during process 540 are examined to determine whether there are any relationships between the VCOs that may be of interest to collision avoidance, motion planning, and/or the like. In some examples, the relationships may include determining whether an overlap and/or proximity below a threshold exists between one or more VCOs associated with the device being controlled and the VCOs of other devices. In some examples, the threshold may be predetermined based on a system configuration and/or dynamically set by an operator and/or the various positions, velocities, geometries, and/or motion goals. The proximity of the VCOs and/or the overlaps may be used to indicate impending collisions that are to be avoided. In some examples, the overlaps may be used to determine one or more virtual displacing forces that may alter the positioning and/or future motion of one or more of the segments of the device being controlled. In some examples, the relationships may indicate an emergency stop situation. In some embodiments, when more than one VCO associated with a segment is subject to relevant relationships with the VCOs of one or more other segments or devices, the cumulative affects of the relationships may be modeled using superposition and/or other techniques for combining the effects of input from multiple sources. In some embodiments, the impacts of the relationships may be at least partially transferred from one segment to another. This may occur, for example, when a virtual displacing force applied to one segment is transferred via a segment joint to an adjoining segment. In some examples, one or more inverse kinematic models may be used to transfer the impacts of the relationships between segments.

At a process 560, a motion plan is adjusted and/or feedback is provided based on the relationships. Based on the relationships detected during process 550, the motion plan for the one or more segments of the device being controlled may be adjusted and/or feedback may be provided. In some examples, the positions and/or motions determined during process 510 may also be used in conjunction with the one or more kinematic models to prepare a motion plan for the one or more segments of the device being controlled. In some examples, the control unit may determine a collision-avoiding path for the one or more segments of the device it is controlling. In some examples, the motion planning may use the geometries and/or properties of the VCOs received during process 540 as no-fly/stay away zones that the VCOs of the segments of the device the control unit is controlling may not overlap. In some examples, distances between the geometries of the VCOs may be kept above a minimum threshold and/or maximized to further reduce the possibility of a collision using the planned paths. In some examples, the distances may be controlled to maintain a desired amount of virtual displacing force with the VCOs associated with other devices. In some examples, the desired amount of virtual displacing force may be zero to implement collision avoidance and/or non-zero to implement coordinated motion. In some examples, the end position of the motion plan may correspond to a desired position and/or orientation of one or more end effectors of the device being controlled. In some examples, the virtual displacing forces determined during process 550 may be used to provide feedback to an operator of the device being controlled. In some examples, the feedback may be provided through a haptic control and/or through visual and/or audio cues. In some examples, the feedback may be mapped back to the end effector and/or the segments of the device being controlled by inducing feedback forces or torques on the joints of the device being controlled. In some examples, the induced feedback forces or torques may modify the forces or torques for the corresponding joints determined from other motion planning and/or operator commanded movements. In some examples, a Jacobian transpose or similar method may be used to map the feedback to the induced feedback forces or torques.

At a process 570, motion is performed. Using the motion plan adjusted during process 560, the control unit may direct one or more movement commands to the actuators of the device being controlled. The one or more actuators may then move the segments of the device being controlled consistent with the motion plan. In some examples, this may include adjusting one or more currents and/or voltages supplied to the actuators.

As the motion plan is being performed during process 570, this may result in changes in the position and/or motion of the segments of the device being controlled. Thus, method 500 may periodically repeat so that the motion being performed is being continually updated to reflect changes in the positions, orientations, and/or movement of each of the segments of the various devices that are relevant to the movement of the device being controlled.

As discussed above and further emphasized here, FIG. 5 is merely an example which should not unduly limit the scope of the claims. One of ordinary skill in the art would recognize many variations, alternatives, and modifications. According to some embodiments, the coordinated motion of method 500 may further include creating one or more VCOs to create one or more protectable regions and/or to reserve one or more operational volumes in the work space. In some examples, the one or more protectable regions may be associated with patient anatomy and/or other objects in the work space. In some examples, the one or more rotectable regions may include geometries that are dynamic.

Some examples of control units, such as the control units 120 and/or 140 may include non-transient, tangible, machine readable media that include executable code that when run by one or more processors (e.g., the processors 122 and/or 142) may cause the one or more processors to perform the processes of methods 300 and/or 500. Some common forms of machine readable media that may include the processes of methods 300 and/or 500 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A control unit comprising:
one or more processors; and
an interface for coupling the control unit to a device;
wherein the control unit is configured to use the one or more processors to:
determine a volume occupied by a first movable segment of the device;
adjust, based on a planned motion of at least the first movable segment of the device, a property of one or more first virtual collision objects (VCOs) approximating the volume;
determine, based on the volume and the adjusted property, one or more first geometries of the one or more first VCOs;
determine a relationship between the one or more first geometries and one or more second geometries of one or more second VCOs of a second segment of a second device;
adjust, based on the relationship, the planned motion; and
control the device according to the adjusted planned motion.

2. The control unit of claim 1, wherein the adjusted planned motion avoids overlapping the one or more first VCOs and the one or more second VCOs.

3. The control unit of claim 1, wherein the property is selected from a group consisting of:
one or more sizes of the one or more first VCOs,
one or more shapes of the one or more first VCOs,
a number of the one or more first VCOs, and
one or more coefficients of resiliency of the one or more first VCOs.

4. The control unit of claim 1, wherein:
the property comprises a coefficient of resiliency of at least one of the one or more first VCOs; and
the control unit is further configured to adjust the coefficient of resiliency based on a corresponding first geometry of the at least one of the one or more first VCOs.

5. The control unit of claim 1, wherein:
the property comprises a coefficient of resiliency of at least one of the one or more first VCOs; and
the control unit is further configured to adjust the coefficient of resiliency based on a direction of motion of the at least one of the one or more first VCOs.

6. The control unit of claim 1, wherein:
the property comprises a size of at least one of the one or more first VCOs; and
the control unit is further configured to adjust the size of the at least one of the one or more first VCOs based on a velocity or a momentum of the first movable segment.

7. The control unit of claim 1, wherein:
the property comprises a number of the one or more first VCOs; and
the control unit is further configured to adjust the number of the one or more first VCOs based on a velocity or a momentum of the first movable segment.

8. The control unit of claim 1, wherein the control unit is further configured to increase a size of at least one of the one or more first VCOs so as to induce a stop in the second device.

9. The control unit of claim 1, wherein the control unit is further configured to increase a size of at least one of the one or more first VCOs so as to induce a retreat in the second device.

10. The control unit of claim 1, wherein the control unit is further configured to create a third VCO to:
reserve an operational volume for the device; or
create a protected region in a workspace reachable by the device.

11. The control unit of claim 1 wherein the control unit is configured to determine the relationship by determining a distance between at least one of the one or more first VCOs and at least one of the one or more second VCOs.

12. A method comprising:
 determining, by a control unit, a volume occupied by a first movable segment of a device;
 adjusting, by the control unit and based on a planned motion of at least the first movable segment of the device, a property of one or more first virtual collision objects (VCOs);
 determining, by the control unit and based on the volume and the property, one or more first geometries of the one or more first VCOs;
 determining, by the control unit, a relationship between the one or more first geometries and one or more second geometries of one or more second VCOs of a second segment of a second device;
 adjusting, by the control unit and based on the relationship, the planned motion; and
 controlling, by the control unit, the device according to the adjusted planned motion.

13. The method of claim 12, wherein the property is selected from a group consisting of:
 one or more sizes of the one or more first VCOs,
 one or more shapes of the one or more first VCOs,
 a number of the one or more first VCOs, and
 one or more coefficients of resiliency of the one or more first VCOs.

14. The method of claim 12, wherein adjusting the property comprises adjusting a coefficient of resiliency for at least one of the one or more first VCOs based on a corresponding first geometry or a direction of motion of the at least one of the one or more first VCOs.

15. The method of claim 12, wherein adjusting the property comprises adjusting a size of at least one of the one or more first VCOs or a number of the one or more first VCOs based on a velocity or a momentum of the first movable segment.

16. The method of claim 12, wherein adjusting the property comprises increasing a size of at least one of the one or more first VCOs so as to induce a stop or a retreat in the second device.

17. The method of claim 12, further comprising creating a third VCO to:
 reserve an operational volume for the device; or
 create a protected region in a workspace reachable by the device.

18. One or more non-transitory machine-readable media comprising a plurality of machine-readable instructions, which, when executed by one or more processors associated with a device, cause the one or more processors to perform the steps of:
 determining a volume occupied by a first movable segment of the device;
 adjusting, based on a planned motion of at least the first movable segment of the device, a property of one or more first virtual collision objects (VCOs);
 determining, based on the volume and the property, one or more first geometries of the one or more first VCOs;
 determining a relationship between the one or more first geometries and one or more second geometries of one or more second VCOs of a second segment of a second device;
 adjusting, based on the relationship, the planned motion; and
 controlling the device according to the adjusted planned motion.

19. The one or more non-transitory machine-readable media of claim 18, wherein adjusting the property comprises adjusting, based on a velocity or a momentum of the first movable segment, a size of at least one of the one or more first VCOs or a number of the one or more first VCOs.

20. The one or more non-transitory machine-readable media of claim 18, wherein the steps further comprise creating a third VCO to:
 reserve an operational volume for the device; or
 create a protected region in a workspace reachable by the device.

* * * * *

UNITED STATES PATENT AND TRADEMARK OFFICE
CERTIFICATE OF CORRECTION

Page 1 of 1

PATENT NO. : 10,849,591 B2
APPLICATION NO. : 15/956463
DATED : December 1, 2020
INVENTOR(S) : Mahdi Azizian et al.

It is certified that error appears in the above-identified patent and that said Letters Patent is hereby corrected as shown below:

On the Title Page

(63) Related U.S. Application Data:
Please delete "Continuation of application No. 15/116,561, filed as application No. PCT/US2015/014395 on Feb. 4, 2015, now Pat. No. 9,993,222." and insert --Continuation of application No. 15/116,561, filed on Aug. 4, 2016, now Pat. No. 9,993,222, which is a 371 of application No. PCT/US2015/014395, filed on Feb. 4, 2015.--.

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*